United States Patent [19]
Doherty

[11] 3,962,263
[45] June 8, 1976

[54] N-(2,2-DIFLUOROALKANOYL)-2,3-PYRIDINEDIAMINE COMPOUNDS

[75] Inventor: George O. P. Doherty, Greenfield, Ind.

[73] Assignee: Eli Lilly and Company, Indianapolis, Ind.

[22] Filed: Dec. 9, 1971

[21] Appl. No.: 206,492

Related U.S. Application Data

[60] Division of Ser. No. 21,536, March 20, 1970, which is a continuation-in-part of Ser. No. 822,042, May 5, 1969.

[52] U.S. Cl. .................. 260/294.9; 260/295 AM; 260/295.5 A; 71/94

[51] Int. Cl.² ..................................... C07D 213/75
[58] Field of Search ............... 260/294.9, 295.5 A, 260/295 AM

[56] References Cited
UNITED STATES PATENTS
3,535,328  10/1970  Zielinski ........................... 260/296

Primary Examiner—G. Thomas Todd
Attorney, Agent, or Firm—Kathleen R. S. Page; Everet F. Smith

[57] ABSTRACT

N-(2,2-Difluoroalkanoyl)-2,3-pyridinediamine compounds useful as herbicides.

7 Claims, No Drawings

N-(2,2-DIFLUOROALKANOYL)-2,3-PYRIDINEDIAMINE COMPOUNDS

CROSS-REFERENCE TO RELATED APPLICATION

This is a division of my co-pending application Ser. No. 21,536, filed Mar. 20, 1970, which was in turn a continuation-in-part of my then copending application Ser. No. 822,042, filed May 5, 1969.

SUMMARY OF THE INVENTION

The present invention is directed to novel N-(2,2-difluoroalkanoyl)-2,3-pyridinediamine compounds of the formula

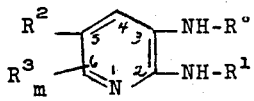

wherein
  one of $R^0$ and $R^1$ represents a 2,2-difluoroalkanoyl radical of the formula

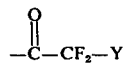

wherein Y represents hydrogen, chlorine, fluorine, perfluoroalkyl of $C_1$-$C_6$, or radical of the formula

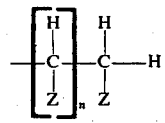

wherein each Z independently represents hydrogen or halogen and n represents 0 or 1; the other of $R^0$ and $R^1$ represents
  hydrogen

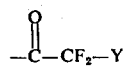

wherein Y is as defined above,
  alkanoyl of $C_1$-$C_8$,
  loweralkenoyl of $C_3$-$C_4$,
  loweralkynoyl of $C_3$-$C_4$,
  halogenated loweralkanoyl of $C_2$-$C_4$ bearing on any position or positions one or more halogen atoms, each independently selected, subject to the limitation that the alpha position bear at least one substituent moiety selected from the group consisting of hydrogen and halogen of atomic weight from 35 to 127, both inclusive,
  radical of the formula

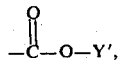

wherein Y' represents loweralkyl of $C_1$-$C_4$ or phenyl,
  benzoyl,
  furoyl,
  naphthoyl, or
  substituted benzoyl of the formula

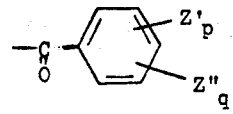

wherein each Z' independently represents halo or nitro, Z" represents loweralkyl of $C_1$-$C_4$ or loweralkoxy of $C_1$-$C_4$, p represents 1 or 2, q represents 0 or 1, and the sum of p and q is 1 or 2;
  $R^2$ represents halogen, nitro, $-CF_3$, $-CF_2Cl$, $-CF_2H$, cyano, or loweralkylsulfonyl of $C_1$-$C_4$;
  $R^3$ represents halogen;
  and m represents an integer of from 0 to 2, both inclusive, subject to the limitation that when $R^2$ represents a moiety other than halogen, m is no greater than 1; and the acid addition salts thereof.

The N-(2,2-difluoroalkanoyl)-2,3-pyridinediamine compounds of the present invention are useful as herbicides. Hence the present invention is directed to methods employing and compositions comprising these novel N-(2,2-difluoroalkanoyl)-2,3-pyridinediamine compounds as herbicides.

DETAILED DESCRIPTION OF THE INVENTION

For the sake of uniformity, starting materials and products herein are named, where possible, as 2,3-pyridinediamines. In accordance with common nomenclature practice, the identification of various substituent positions is as follows:

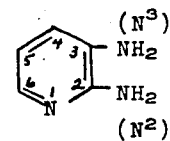

In the foregoing definition of the compounds of the present invention, as generally in the present specification and claims, each of the terms "halo" and "halogen," when unqualified but as used both alone and in the composite term "halogenated loweralkanoyl," designates bromine, chlorine, fluorine, or iodine, only.

An essential and distinguishing structural feature of the compounds of the present invention is the 2,2-difluoroalkanoyl radical ($R^0$ or $R^1$); representative 2,2-difluoroalkanoyl radicals include the following:
  difuoroacetyl
  trifluoroacetyl
  difluorochloroacetyl
  pentafluoropropionyl
  heptafluorobutyryl
  nonafluorovaleryl
  undecafluorohexanoyl
  tridecafluoroheptanoyl
  pentadecafluorooctanoyl
  2,2-difluoropropionyl
  2,2-difluorobutyryl
  2,2-difluoro-3-bromopropionyl
  2,2-difluoro-3-chloropropionyl
  2,2-difluoro-3,4-dichlorobutyryl
  2,2-difluoro-4-bromobutyryl
  2,2,3-trifluoropropionyl 2,2,3-trifluorobutyryl
2,2,3,4-tetrafluorobutyryl
2,2-difluoro-3-bromo-4-chlorobutyryl
2,2-difluoroalkanoyl Preferred 2,2-difluoroalkanoyl groups are trifluoroacetyl, difluoroacetyl, and difluorochloroacetyl.

The compounds of the present invention are prepared by introduction of the characteristic 2,2-difluoroalkanoyl group into appropriate corresponding diamine starting materials. Introduction of this group can be achieved by any of numerous available acylation reactions, employing any of several types of acylating agent. The identity of acylating agent is not critical; suitable acylating agents include the 2,2-difluoroalkanoyl halides:

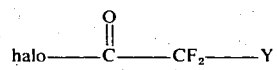

and the 2,2-difluoroalkanoic anhydrides:

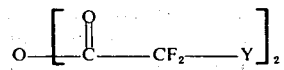

The diamine starting materials with which the acylating reaction is carried out will vary. In the instance of compounds of the present invention bearing only one 2,2-difluoroalkanoyl radical or bearing two identical 2,2-difluoroalkanoyl radicals ($R^1 = R^0$), the starting diamine is a compound of the formula

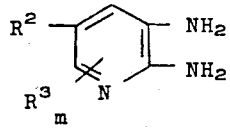

and either one acyl group is introduced (leaving one of $R^0$ and $R^1$ = hydrogen) or two identical acyl groups are introduced

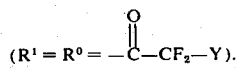

Where, on the other hand, $R^1$ is any other moiety than hydrogen or the same 2,2-difluoroalkanoyl moiety as is represented by $R^0$, the appropriate diamine starting material is a compound already bearing the desired other moiety, and the characteristic 2,2-difluoroalkanoyl group is similarly introduced by acylation. It is noted that one of $R^0$ and $R^1$ can be a 2,2-difluoroalkanoyl group different from that represented by the other of $R^0$ and $R^1$, in which instance the groups are introduced sequentially.

While the synthetic routes described foregoing are convenient are preferred, yet other routes can be utilized. Thus, for example, in the instance where one of $R^0$ and $R^1$ represents an acyl group other than a 2,2-difluoroalkanoyl radical, such other group is conveniently introduced in some instances after the 2,2-difluoroalkanoyl moiety has already been introduced. However, because of the activating effect on acylation of the alpha fluorine atoms, it is generally preferred that groups other than the 2,2-difluoroalkanoyl moiety already be present when the group is introduced. In the instance where $R^1$ = formyl, the acylation is conducted with mixed anhydride of acetic/formic acid. Alternately, other acylating agents by which formyl groups are introduced can be used.

The preparation of amides by the acylation of corresponding amines with various acylating agents is, as noted, a known synthetic method. The present preparations are conducted in accordance with the known procedures for effecting this method. Thus, where the acylating agent is an anhydride, the reaction is conveniently conducted at room temperature; solvent, which can be excess anhydride, can be utilized. Where an acyl halide is employed as acylating agent, the reaction is necessarily conducted in the presence of an inert solvent, and the reaction mixture is preferably cooled, such as to temperatures of 0°–10°C. In the case of either acylating agent, the produce is separated in conventional procedures, and can be purified if desired, likewise in conventional procedures.

The following examples illustrate the synthesis of the compounds of the present invention and will enable those skilled in the art to practice the present invention.

EXAMPLE 1:
$N^2,N^3$-BIS(TRIFLUOROACETYL)-5-CHLORO-2,3)PYRIDINEDIAMINE

5-Chloro-2,3-pyridinediamine (1.43 grams) was mixed with 30 milliliters of chloroform and 2 milliliters of triethylamine, and the resulting mixture stirred while a second mixture of 3 milliliters of trifluoroacetic anhydride in 10 milliliters of chloroform was added portionwise over a period of fifteen minutes. The addition was carried out at 25°C. and the resulting reaction mixture permitted to stand for a period of time and then filtered to separate the desired $N^2,N^3$-bis(trifluoroacetyl)-5-chloro-2,3-pyridinediamine product. It was recrystallized from chloroform, m.p., 176°C. (subliming from 160°C.).

EXAMPLE 2:
$N^3$-TRIFLUOROACETYL-5-CHLORO-2,3-PYRIDINEDIAMINE

5-Chloro-2,3-pyridinediamine (2.8 grams) was dissolved in 50 milliliters of tetrahydrofuran and 2.02 milliliters of triethylamine and the solution treated with trifluoroacetyl chloride (2.6 grams) in 100 milliliters of tetrahydrofuran. The addition was carried out at room temperature over a period of 2 hours, and the reaction mixture was then held at room temperature for another hour with stirring. Solvent was removed by evaporation, and the residue recrystallized from a chloroform/acetone mixture to obtain the desired $N^3$-trifluoroacetyl-5-chloro-2,3-pyridinediamine product, m.p., 292°–93°C.

EXAMPLES 3–42:

Other compounds representative of the present invention are readily prepared in the procedures of the foregoing teachings and examples, using analogous starting materials. Such compounds include the following:

$N^3$-Difluorochloroacetyl-5-chloro-2,3-pyridinediamine, m.p., 360°C., prepared by reacting difluorochloroacetic anhydride with 5-chloro-2,3-pyridinediamine.

$N^3$-Trifluoroacetyl-5-nitro-2,3-pyridinediamine, prepared by reacting trifluoroacetic anhydride with 5-nitro-2,3-pyridinediamine.

$N^2,N^3$-Bis(difluoroacetyl)-4,5-dibromo-2,3-pyridinediamine, prepared by reacting difluoroacetic anhydride with 4,5-dibromo-2,3-pyridinediamine.

$N^2$-Propionyl-$N^3$-(2,2-difluoro-3-iodopropionyl)-5-(secbutylsulfonyl)-2,3-pyridinediamine, prepared by reacting 2,2-difluoro-3-iodopropionyl chloride with $N^2$-propionyl-b 5-(secbutylsulfonyl)-2,3-pyridinediamine.

$N^3$-Trifluoroacetyl-$N^2$-acetyl-5-bromo-2,3-pyridinediamine, prepared by reacting trifluoroacetic anhydride with $N^2$-acetyl-5-bromo-2,3-pyridinediamine.

$N^2$-Trifluoroacetyl-$N^3$-furoyl-5-chloro-2,3-pyridinediamine, prepared by reacting trifluoroacetic anhydride with $N^3$-furoyl-5-chloro-2,3-pyridinediamine.

$N^2$-Butyryl-$N^3$-(2,2-difluoro-3,4-dichlorobutyryl)-5,6-dichloro-2,3-pyridinediamine, prepared by reacting 2,2-difluoro3,4-dichlorobutyric anhydride with $N^2$-butyryl-5,6-dichloro-2,3-pyridinediamine.

$N^3$-(2,2,3-Trifluoropropionyl)-$N^2$-octanoyl-5-fluoro-2,3-pyridinediamine, prepared by reacting 2,2,3-trifluoropropionic anhydride with $N^2$-octanoyl-5-fluoro-2,3-pyridinediamine.

$N^2,N^3$-Bis(trifluoroacetyl)-5-(methylsulfonyl)-2,3-pyridinediamine, prepared by reacting trifluoroacetic anhydride with 5-(methylsulfonyl)-2,3-pyridinediamine.

$N^2,N^3$-Bis(2,2-difluorobutyryl)-5-chloro-2,3-pyridinediamine, prepared by reacting 2,2-difluorobutyric anhydride with 5-chloro-2,3-pyridinediamine.

$N^3$-Trifluoroacetyl-$N^2$-p-toluoyl-5,6-dichloro-2,3-pyridinediamine, prepared by reacting trifluoroacetyl chloride with $N^2$-p-toluoyl-5,6-dichloro-2,3-pyridinediamine.

$N^2$-Acetyl-$N^3$-trifluoroacetyl-5-(methylsulfonyl)-2,3-pyridinediamine, prepared by reacting trifluoroacetic anhydride with $N^2$-acetyl-5-(methylsulfonyl)-2,3-pyridinediamine.

$N^3$-(2,2-Difluoro-3-chloropropionyl)-$N^2$-acryloyl-4,5,6-trichloro-2,3-pyridinediamine, prepared by reacting 2,2-difluoro-3-chloropropionic anhydride with $N^2$-acryloyl-4,5,6-trichloro-2,3-pyridinediamine.

$N^3$-Difluorochloroacetyl-$N^2$-hexanoyl-5-(n-propylsulfonyl)-2,3-pyridinediamine, prepared by reacting difluorochloroacetic anhydride with $N^2$-hexanoyl-5-(n-propylsulfonyl)-2,3-pyridinediamine.

$N^2$-Trifluoroacetyl-$N^3$-(pentadecafluorooctanoyl)-5-bromo-2,3-pyridinediamine, prepared by reacting trifluoroacetic anhydride with $N^3$-(pentadecafluorooctanoyl)-5-bromo-2,3-pyridinediamine.

$N^3$-Difluorochloroacetyl-$N^2$-(nonafluorovaleryl)-5-trifluoromethyl-2,3-pyridinediamine, prepared by reacting difluorochloroacetic anhydride with $N^2$-(nonafluorovaleryl)-5-trifluoromethyl-2,3-pyridinediamine.

$N^2$-Propioloyl-$N^3$-(2,2-difluoro-3-bromo-4-chlorobutyryl)-5-difluorochloromethyl-2,3-pyridinediamine, prepared by reacting 2,2-difluoro-3-bromo-4-chlorobutyryl chloride with $N^2$-propioloyl-5-difluorochloromethyl-2,3-pyridinediamine.

$N^2,N^3$-Bis(2,2-difluoro-4-bromobutyryl)-5-nitro-2,3-pyridinediamine, prepared by reacting 2,2-difluoro-4-bromobutyric anhydride with 5-nitro-2,3-pyridinediamine.

$N^2$-Acetyl-$N^3$-trifluoroacetyl-5-trifluoromethyl-2,3-pyridinediamine, prepared by reacting trifluoroacetic anhydride with $N^2$-acetyl-5-trifluoromethyl-2,3-pyridinediamine.

$N^3$-(3-Bromopropionyl)-$N^2$-trifluoroacetyl-5-(ethylsulfonyl)-2,3-pyridinediamine, prepared by reacting trifluoroacetic anhydride with $N^3$-(3-bromopropionyl)-5-(ethylsulfonyl)-2,3-pyridinediamine.

$N^2$-Trifluoroacetyl-$N^3$-(p-methoxybenzoyl)-5-cyano-2,3-pyridinediamine, prepared by reacting trifluoroacetic anhydride with $N^3$-(p-methoxybenzoyl)-5-cyano-2,3-pyridinediamine.

$N^2$-(2,2-Difluoropropionyl)-$N^3$-(4-chlorobutyryl)-5,6-dichloro-2,3-pyridinediamine, prepared by reacting 2,2-difluoropropionic anhydride with $N^3$-(4-chlorobutyryl)-5,6-dichloro-2,3-pyridinediamine.

$N^3$-Trifluoroacetyl-$N^2$-(methoxycarbonyl)-5,6-difluoro-2,3-pyridinediamine, prepared by reacting trifluoroacetic anhydride with $N^2$-(methoxycarbonyl)-5,6-difluoro-2,3-pyridinediamine.

$N^2$-Difluorochloroacetyl-$N^3$-(phenoxycarbonyl)-5-nitro-2,3-pyridinediamine, prepared by reacting difluorochloroacetic anhydride with $N^3$-(phenoxycarbonyl)-5-nitro-2,3-pyridinediamine.

$N^1,N^2$-Bis(trifluoroacetyl)-5-chloro-2,3-pyridinediamine, prepared by reacting trifluoroacetic anhydride with 5-chloro-2,3-pyridinediamine.

$N^3$-(3,4-Dichlorobenzoyl)-$N^2$-difluoroaetyl-5-chloro-2,3-pyridinediamine, prepared by reacting difluoroacetic anhydride with $N^3$-(3,4-dichlorobenzoyl)-5-chloro-2,3-pyridinediamine.

$N^3$-Pentafluoropropionyl-$N^2$-(5-bromo-m-toluoyl)-4,5,6-trichloro-2,3-pyridinediamine, prepared by reacting pentafluoropropionic anhydride with $N^2$-(5-bromo-m-toluoyl)-4,5,6-trichloro-2,3-pyridinediamine.

$N^2,N^3$-Bis(trifluoroacetyl)-5-fluoro-2,3-pyridinediamine, prepared by reacting trifluoroacetic anhydride with 5-fluoro-2,3-pyridinediamine.

$N^3$-(3,5-Dinitrobenzoyl)-N-difluorochloroacetyl-5-chloro-2,3-pyridinediamine, prepared by reacting difluorochloroacetyl chloride with $N^3$-(3,5-dinitrobenzoyl)-5-chloro-2,3-pyridinediamine.

$N^3$-Heptafluorobutyryl-$N^2$-(sec-butoxycarbonyl)-5-bromo-2,3-pyridinediamine, prepared by reacting heptafluorobutyric anhydride with $N^2$-(sec-butoxycarbonyl)-5-bromo-2,3-pyridinediamine.

$N^2$-(2-Butenoyl)-$N^3$-difluorochloroacetyl-5-(methylsulfonyl)-2,3-pyridinediamine, prepared by reacting difluorochloroacetic anhydride with $N^2$-(2-butenoyl)-5-(methylsulfonyl)-2,3-pyridinediamine.

$N^2$-(2,2-Difluoropropionyl)-$N^3$-(3-nitro-5-isopropoxybenzoyl)-5,6-dichloro-2,3-pyridinediamine, prepared by reacting 2,2-difluoropropionyl bromide with $N^3$-(3-nitro-5-isopropoxybenzoyl)-5,6-dichloro-2,3-pyridinediamine.

$N^3$-Naphthoyl-$N^2$-trifluoroacetyl-5-nitro-2,3-pyridinediamine, prepared by reacting trifluoroacetic anhydride with $N^3$-naphthoyl-5-nitro-2,3-pyridinediamine.

$N^2$-(3-Fluoropropionyl)-$N^3$-trifluoroacetyl-5-cyano-2,3-pyridinediamine, prepared by reacting trifluoroacetic anhydride with $N^2$-(3-fluoropropionyl)-5-cyano-2,3-pyridinediamine.

$N^2,N^3$-Bis(difluoroacetyl)-5-difluoromethyl-2,3-pyridinediamine, prepared by reacting difluoroacetic anhydride with 5-difluoromethyl-2,3-pyridinediamine.

$N^2,N^3$-Bis(trifluoroacetyl)-5-cyano-2,3-pyridinediamine, prepared by reacting trifluoroacetic anhydride with 5-cyano-2,3-pyridinediamine.

$N^3$-Iodoacetyl-$N^2$-trifluoroacetyl-5-(methylsulfonyl)-2,3-pyridinediamine, prepared by reacting trifluoroacetic anhydride with $N^3$-iodoacetyl-5-(methylsulfonyl)-2,3-pyridinediamine.

$N^3$-Difluoroacetyl-5-chloro-2,3-pyridinediamine, prepared by reacting difluoroacetic anhydride with 5-chloro-2,3-pyridinediamine.

$N^3$-Trifluoroacetyl-$N^2$-(2,3-dichloropropionyl)-5-iodo-2,3-pyridinediamine, prepared by reacting trifluoroacetic anhydride with $N^2$-(2,3-dichloropropionyl)-5-iodo-2,3-pyridinediamine.

$N^2$-Bromoacetyl-$N^3$-trifluoroacetyl-5-nitro-2,3-pyridinediamine, prepared by reacting trifluoroacetic anhydride with $N^2$-bromoacetyl-5-nitro-2,3-pyridinediamine.

The compounds of the present invention are adapted to be employed as herbicides. The compounds can be utilized to achieve broad herbicidal action; hence, in its broadest sense, the present invention is directed to a method which comprises applying to a plant part, which can be a stem, leaf, flower, fruit, root, or seed or other similar reproductive unit of a plant, a growth-inhibiting amount of one of the N-(2,2-difluoroalkanoyl)-2,3-pyridinediamine compounds of the present invention. However, the compounds can also be utilized to take advantage of selective patterns of herbicidal activity.

It is not critical to the practice of the present invention that complete destruction of undesirable vegetation be obtained, it being adequate if the growth of the unwanted vegetation is merely inhibited. Especially where selective action is sought, inhibition falling short of actual killing is adequate, particularly when combined with naturally occurring conditions such as limited moisture and the like which more adversely affect the vegetation selectively inhibited than the crop plant.

The compounds of the present invention are suited to a wide variety of herbicidal application. Thus, for example, at rates which evoke the selective action of the compounds, which rates are defined more completely hereinbelow, the compounds can be used as selective herbicides in crop plants, such as, for example, cotton, corn, sorghum, soybeans, and the like. In such use, application can be made preemergent to both crops and weeds, or, preferably by means of a directed spray application technique, postemergent to the crop plant but both preemergent and postemergent to the weeds. In another application, the compounds can be used to give broad herbicidal action on non-crop land, including intermittently non-crop strips of contour-farmed land. For such usage on so-called fallow land, application can be made in spring to suppress vegetative growth until a fall or following spring planting or the fall to suppress vegatative growth until a spring or following fall planting. Furthermore, in another application, the present compounds can be utilized to control weeds in tree crop plantings, such as plantings of the various citrus trees. In addition to the foregoing terrestial embodiments, the present compounds can also be utilized as aquatic herbicides.

The practice of the present invention in any of its numerous embodiments can in some instances be carried out with unmodified compound; however, for good results, it is generally necessary that the compound be employed in modified form, that is, as one component of a composition formulated to implement the plant growth-inhibiting effects. Thus, for example, the active agent can be mixed with water or other liquids, preferably aided by the usage of a surface active agent. The active agent can also be incorporated on a finely divided solid, which can be a surface active substance, to yield a wettable powder, which can subsequently be dispersed in water or other liquid or incorporated as part of a dust which can be applied directly. Other methods of formulations are known in the art and can be employed in implementing the present invention.

In carrying out the novel method of the present invention, the exact amount of the active agent employed is not critical and will vary, depending upon the type of growth-inhibiting effect desired, the identity of the plants concerned, the particular active agent used, weather conditions, and the like. In general, broad growth-inhibiting effect is obtained with rates of from 0.5 to 20 pounds or more of active agent per acre, and such rates are suitable and effective for control of vegetative growth on fallow land. When it is desired to obtain a selective growth-inhibiting effect on weeds in areas containing crop plants such as corn, soybeans, and cotton, rates of from 0.5 to 10 pounds generally give good results. When in the typical mode of operation, the active agent is employed as a composition comprising the agent, the exact concentration of active agent in the composition is not critical, except that the concentration and total amount of formulation employed be adequate to supply the appropriate amount of active agent on a per acre basis. In general, good results are obtained when employing formulations containing the active agent in a concentration of from 0.5 to 10 percent or higher, in the instance of a liquid formulation; and in a concentration of from 1.0 to 5.0 percent or higher, in the instance of a dust, powder, granule, or the like. More concentrated formulations can be prepared and are often preferred in that they can serve, depending upon the particular application contemplated and the particular concentration, both as a concentrated formulation for purposes of shipment, storage, and the like, and as an ultimate treating composition. Thus, for example, formulations often preferably contain a surface active agent and the present active agent, the latter being present in an amount of from 0.5 to 99.5 percent, by weight; or an inert, finely divided solid and the present active agent, the latter being present in an amount of from 1.0 to 99 percent, by weight. Such formulations, as indicated, can be employed directly in certain applications, but can also be diluted and subsequently employed in many other applications.

Liguid compositions containing the desired amount of active agent are prepared by dissolving the substance in an organic liquid or by dispersing the substance in water with or without the aid of a suitable surface active dispersing agent, such as an ionic or non-ionic emulsifying agent. Such compositions can also contain modifying substances which serve as a "spreader" and "sticker" on plant foliage. Suitable organic liquid carriers include the agricultural spray oils and the petroleum distillates such as diesel fuel, kerosene, fuel oil naphthas and Stoddard solvent. Among such liquids the petroleum distillates are generally preferred. The aqueous compositions can contain one or more water immiscible solvents for the toxicant compound. In such compositions, the carrier comprises an aqueous emulsion, e.g., a mixture of water, emulsifying agent and water immiscible solvent. The choice of dispersing and emulsifying agent and the amount thereof employed is dictated by the nature of the composition and by the ability of the agent so facilitate the dispersion of the active agent in the carrier to produce the desired composition. Dispersing and emulsifying agents which can be employed in the compositions include the condensation products of alkylene oxides with phenols and organic acids, alkyl aryl sulfonates, polyoxyalkylene derivatives or sorbitan esters, complex ether alcohols, and the like. Representative surface active agents which are suitably employed in implementing the present invention are identified in U.S. Pat. Nos. 3,095,299, second column, lines 25–36; 2,665,447, column 5; and 2,412,510, columns 4 and 5.

In the preparation of dust compositions, the active ingredient is intimately dispersed in and on a finely divided solid such as clay, talc, chalk, gypsum, limestone, vermiculite fines, perlite, and the like. In one method of achieving such dispersion, the finely divided carrier is mechanically mixed or ground with the active agent.

Similarly, dust compositions containing the toxicant compounds can be prepared with various of the solid surface active dispersing agents such as bentonite, fuller's earth, attapulgite and other clays. Depending upon the proportions of ingredients, these dust compositions can be employed as concentrates and subsequently diluted with additional solid surface active dispersing agents or with chalk, talc, or gypsum and the like to obtain the desired amount of active ingredient in a composition adapted to be employed for the suppression of the growth of the plants. Also, such dust compositions can be dispersed in water, with or without the aid of a dispersing agent, to form spray mixtures.

Formulations containing the present active agent are often advantageously further modified by incorporation therein of an effective amount of a surfactant which facilitates the dispersion and spreading of the formulation on the plant leaf surfaces and the incorporation of the formulation by the plant.

In accordance with the present invention, the active agent can be dispersed in soil or other growth media in any convenient fashion. Applications can be carried out by simply mixing with the media, by applying to the surface of soil and thereafter dragging or discing into the soil to the desired depth, or by employing a liquid carrier to accomplish the penetration and impregnation. The application of spray and dust compositions to the surface of soil, or to plant parts or the above ground surfaces of plants can be carried out by conventional methods, e.g., powder dusters, boom and hand sprayers and spray dusters, whether surface or air-borne.

In a further method, the distribution of the active agent in soil can be accomplished by introducing the agent into the water employed to irrigate the soil. In such procedures, the amount of water is varied with the porosity and water-holding capacity of the soil to obtain a desired depth of distribution of the agent.

In addition, the present method also comprehends the employment of an aerosol composition containing one or more of the present active agents as an active compound. Such a composition is prepared according to conventional methods wherein the agent is dispersed in a solvent, and the resultant dispersion mixed with a propellent in liquid state. Such variables as the particular agent to be used and the nature of the vegetation which is to be treated will determine the desirability of the solvent and concentration of the agent therein. Examples of suitable solvents are water, acetone, isopropanol, and 2-ethoxyethanol.

Satisfactory results are obtained when the active agent of the present invention, or a composition comprising such active agent, is combined with other agricultural materials intended to be applied to plants, plant parts, or their habitats. Such materials include fertilizers, fungicides, insecticides, other herbicides, soil conditioning agents, and the like.

EXAMPLES 43–44:

$N^3$-Trifluoroacetyl-5-chloro-2,3-pyridinediamine and $N^2,N^3$-bis(trifluoroacetyl)-5-chloro-2,3-pyridinediamine were evaluated for preemergent application to various species of plants. In this elevation, a soil was prepared consisting of one part masonry sand and one part shredded top soil blended together in a cement mixer. One gallon of this soil was placed in a 25 × 35 cm. galvanized flat and was patted down with a bench brush until level. A three-row marker was used to make 2½ cm. deep furrows in approximately two-fifths of the flat. Crop seeds consisting of four kernels of corn, five cotton seeds and five soybean seeds were placed in these furrows. A four-row template was then placed on the remaining soil and the indicated approximate numbers of each of the following seeds were planted, one species to each section: foxtail (millet), 80–100 seeds; velvetleaf (40–50 seeds); rough pigweed (150–250 seeds); and large crabgrass (100–150 seeds).

Sufficient soil was added to cover the entire flat. Thus, the weed seeds were covered to a depth of about 6 mm. and the crop seeds were covered to a depth of about 3 cm.

In assaying the effect of the compositions as preemergent herbicides, a flat prepared as above, taken either on the day of planting or on the next day, was placed in a chamber equipped with a turntable and an air exhaust. The herbicidal composition, either a spray-type emulsion or a wettable powder, was applied to the flat with a modified DeVilbiss atomizer hooked to an air source. Twelve and one-half milliliters of the composition under test were applied to each flat either on the day of planting or on the succeeding day. Injury ratings and observations as to type of injury were made 11 to 12 days after treatment. The injury rating scale used was as follows:

0--no injury
1--slight injury
2--moderate injury
3--severe injury
4--death

When more than one determination was carried out at a given rate, an average value was calculated for the injury rating. Each compound evaluated was formulated as a spray by one of the following procedures. In one method the particular compound was wetted by grinding in a mortar with one part of polyoxyethylene sorbitan monolaurate. Five hundred parts of water were added slowly to the resultant creamy paste to give an aqueous dispersion with a surfactant concentration of 0.2 percent. This dispersion was entirely satisfactory for spray application. In a second procedure the compound was dissolved in one volume of acetone, and the acetone solution was diluted with nineteen volumes of water containing 0.1 percent of polyoxyethylene sorbitan monolaurate.

In the following table setting forth the results of the evaluation, column 1 gives the name of the compound under test; column 2, the rate in pounds per acre at which the compound was applied to the test flat; and the remaining columns, the injury to the particular plant seeds or seedlings as measured by the foregoing scale.

TABLE I

| Compound | Lbs./Acre | Corn | Cotton | Soybean | Crabgrass | Pigweed | Foxtail | Velvet Leaf |
|---|---|---|---|---|---|---|---|---|
| Injury Rating on Preemergent Treatment | | | | | | | | |
| $N^2,N^3$-Bis(trifluoroacetyl)-5-chloro-2,3-pyridinediamine | 8 | 0 | 0 | 0 | 3 | 2 | 2 | 2 |
| $N^3$-Trifluoroacetyl-5-chloro-2,3-pyridinediamine | 4 | 0 | 2 | 1 | 4 | 4 | 3 | 2 |
|  | 2 | 0 | 0 | 0 | 3 | 3 | 3 | 2 |

EXAMPLES 45–46:

$N^2,N^3$-Bis(trifluoroacetyl)-5-chloro-2,3-pyridinediamine and $N^3$-difluorochloroacetyl-5-chloro-2,3-pyridinediamine were also evaluated for postemergent application to plants including corn and several weed species. The evaluation was carried out in accordance with the procedures of Examples 43–44 except that the test solutions were applied about 9–12 days after the preparation and seeding of the flats. The results are as set forth in the following table:

TABLE II

| Compound | Lbs./Acre | Corn | Crabgrass | Pigweed | Foxtail | Velvet Leaf |
|---|---|---|---|---|---|---|
| Injury Rating on Postemergent Treatment | | | | | | |
| $N^2,N^3$-Bis(trifluoroacetyl)-5-chloro-2,3-pyridinediamine | 8 | 0 | 4 | 4 | 4 | 4 |
|  | 4 | 0 | 4 | 4 | 4 | 4 |
|  | 2 | 0 | 4 | 4 | 4 | 3 |
|  | 1 | 0 | 3 | 4 | 3 | 4 |
| $N^3$-Difluorochloroacetyl-5-chloro-2,3-pyridinediamine | 8 | 1 | 3 | 4 | 3 | 4 |

EXAMPLES 47–85:

Essentially the same results as those reported in foregoing Examples 43–46 are obtained when evaluating the following other representative compounds of the present invention:

$N^3$-Trifluoroacetyl-5-nitro-2,3-pyridinediamine
$N^2,N^3$-Bis(difluoroacetyl)-4,5-dibromo-2,3-pyridinediamine
$N^2$-Propionyl-$N^3$-(2,2-difluoro-3-iodopropionyl-5-(sec-butylsulfonyl)-2,3-pyridinediamine
$N^3$-Trifluoroacetyl-$N^2$-acetyl-5-bromo-2,3-pyridinediamine
$N^2$-Trifluoroacetyl-$N^3$-furoyl-5-chloro-2,3-pyridinediamine
$N^2$-Butyryl-$N^3$-(2,2-difluoro-3,4-dichlorobutyryl)-5,6-dichloro-2,3-pyridinediamine
$N^3$-(2,2,3-Trifluoropropionyl)-$N^2$-octanoyl-5-fluoro-2,3-pyridinediamine
$N^2,N^3$-Bis(trifluoroacetyl)-5-(methylsulfonyl)-2,3-pyridinediamine
$N^2,N^3$-Bis(2,2-difluorobutyryl)-5-chloro-2,3-pyridinediamine
$N^3$-Trifluoroacetyl-$N^2$-p-toluoyl-5,6-dichloro-2,3-pyridinediamine
$N^2$-Acetyl-$N^3$-trifluoroacetyl-5-(methylsulfonyl)-2,3-pyridinediamine
$N^3$-(2,2-Difluoro-3-chloropropionyl)-$N^2$-acryloyl-4,5,6-trichloro-2,3-pyridinediamine
$N^3$-Difluorochloroacetyl-$N^2$-hexanoyl-5-(n-propylsulfonyl)-2,3-pyridinediamine
$N^2$-Trifluoroacetyl-$N^3$-(pentadecafluorooctanoyl)-5-bromo-2,3-pyridinediamine
$N^3$-Difluorochloroacetyl-$N^2$-(nonafluorovaleryl)-5-trifluoromethyl-2,3-pyridinediamine
$N^2$-Propioloyl-$N^3$-(2,2-difluoro-3-bromo-4-chlorobutyryl)-5-difluorochloromethyl-2,3-pyridinediamine
$N^2,N^3$-Bis(2,2-difluoro-4-bromobutyryl)-5-nitro-2,3-pyridinediamine
$N^2$-Acetyl-$N^3$-trifluoroacetyl-5-trifluoromethyl-2,3-pyridinediamine
$N^3$-(3-Bromopropionyl)-$N^2$-trifluoroacetyl-5-(ethylsulfonyl)-2,3-pyridinediamine
$N^2$-Trifluoroacetyl-$N^3$-(p-methoxybenzoyl)5-cyano-2,3-pyridinediamine
$N^2$-(2,2-Difluoropropionyl)-$N^3$-(4-chlorobutyryl)-5,6-dichloro-2,3-pyridinediamine
$N^3$-Trifluoroacetyl-$N^2$-(methoxycarbonyl)-5,6-difluoro-2,3-pyridinediamine
$N^2$-Difluorochloroacetyl-$N^3$-(phenoxycarbonyl)-5-nitro-2,3-pyridinediamine
$N^1,N^2$-Bis(trifluoroacetyl)-5-chloro-2,3-pyridinediamine
$N^3$-(3,4-Dichlorobenzoyl)-$N^2$-difluoroacetyl-5-chloro-2,3-pyridinediamine
$N^3$-Pentafluoropropionyl-$N^2$-(5-bromo-m-toluoyl)-4,5,6-trichloro-2,3-pyridinediamine
$N^2,N^3$-Bis(trifluoroacetyl)-5-fluoro-2,3-pyridinediamine
$N^3$-(3,5-Dinitrobenzoyl)-N-difluorochloroacetyl-5-chloro-2,3-pyridinediamine
$N^3$-Heptafluorobutyryl-$N^2$-(sec-butoxycarbonyl)-5-bromo-2,3-pyridinediamine
$N^2$-(2-Butenoyl)-$N^3$-difluorochloroacetyl-5-(methylsulfonyl-2,3-pyridinediamine
$N^2$-(2,2-Difluoropropionyl)-$N^3$-(3-nitro-5-isopropoxybenzoyl)-5,6-dichloro-2,3-pyridinediamine N³-Naphthoyl-N²-trifluoroacetyl-5-nitro-2,3-pyridinediamine N²-(3-Fluoropropionyl)-N³-trifluoroacetyl-5-cyano-2,3-pyridinediamine N²,N³-Bis(difluoroacetyl)-5-difluoromethyl-2,3-pyridinediamine N²,N³-Bis(trifluoroacetyl)-5-cyano-2,3-pyridinediamine N³-Iodoacetyl-N²-trifluoroacetyl-5-(methylsulfonyl)-2,3-pyridinediamine N³-Difluoroacetyl-5-chloro-2,3-pyridinediamine N³-Trifluoroacetyl-N²-(2,3-dichloropropionyl)-5-iodo-2,3-pyridinediamine N²-Bromoacetyl-N³-trifluoroacetyl-5-nitro-2,3-pyridinediamine The starting materials to be employed in accordance with the present invention are prepared in known procedures, and some of them are commercially available. Those starting materials which are of the formula

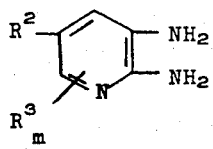

are prepared by a plurality of synthetic steps as are necessary to introduce the required moieties. Most conveniently, one or both of the $NH_2$ groups are introduced by conversion of a halo group. Also, the amino group or groups can be introduced by nitration and subsequent reduction. These various synthetic steps are generally and most conveniently carried out with starting materials already bearing the requisite $R^2$ and $R^3$ moieties. However, it is sometimes suitable that these substituents, where, e.g., nitro or halo, be introduced simultaneously with the synthetic steps leading to the introduction of the amino groups.

Those of the compounds of the present invention wherein $R^1$ is a moiety other than hydrogen or the same acyl moiety as $R^0$, are generally prepared from diamine starting materials already bearing the requisite $R^1$ moiety. These starting materials are themselves prepared from the corresponding diamine starting materials described above by reaction with an appropriate acyl halide, or, in the instance of $R^1$ representing

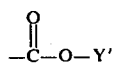

with an appropriate loweralkyl or phenyl haloformate. Alternately, however, these starting materials can be prepared from nitropyridineamine:

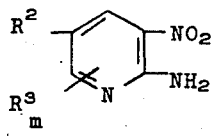

to introduce by acylation a moiety other than a 2,2-difluoroalkanoyl radical followed by reduction and subsequent acylation of the free amino group with a 2,2-difluoroalkanoyl group. All of these reactions are carried out by procedures well known in the prior art.

In representative procedures, 2-amino-5-chloropyridine (100 grams) was dissolved in 390 milliliters of concentrated sulfuric acid. The solution thus obtained was added to 55°C. and concentrated nitric acid (52 milliliters) added portionwise over a period of time and with heating to maintain the temperature of the resulting solution at 55°C. The mixture was then allowed to stir for an additional hour at 55°C. and subsequently poured over 2-3 kilograms of ice and neutralized with 600 milliliters of a 40 percent solution of sodium hydroxide. The desired 2-amino-3-nitro-5-chloropyridine separated as a yellow powder. Additional water was added to make 3 liters of solution and the product was separated and purified by resuspension in 500 milliliters of water. The product thus obtained was dried overnight at 60°C., m.p., 191°–94°C.

Thereafter, 0.1 gram of palladium on carbon was prehydrogenated with 100 milliliters of ethanol as solvent and 1.73 grams of the 2-amino-3-nitro-5-chloropyridine added and hydrogenated. The alcohol was driven off under vacuum and the resulting 5-chloro-2,3-pyridinediamine product recrystallized from water after treatment with activated carbon, m.p., 173°–74°C.

The preparation of the pyridinediamines or nitropyridineamines is carried out in known procedures, and certain of these are known compounds. For a review of the procedures, attention is directed to *Pyridine and its Derivatives*, Vols. 1–4, ed. by Edwin Klingsbert (Interscientific Publishers, Inc., N.Y., 1960).

Particularly preferred compounds in accordance with the present invention are those of the formula

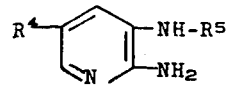

wherein $R^4$ represents halo, $-CF_3$, methylsulfonyl, or cyano; and $R^5$ represents trifluoroacetyl, difluoroacetyl, or difluorochloroacetyl.

I claim:

1. A compound of the formula

wherein
one of $R^0$ and $R^1$ represents a 2,2-difluoroalkanoyl radical of the formula

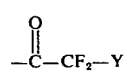

wherein Y represents hydrogen, chlorine, fluorine, perfluoroalkyl of $C_1$–$C_6$, or radical of the formula

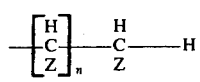

wherein each Z independently represents hydrogen or halogen and n represents 0 or 1;

the other of $R^0$ and $R^1$ represents hydrogen,

wherein Y is as defined above,
alkanoyl of $C_1$–$C_8$,
loweralkenoyl of $C_3$–$C_4$,
loweralkanoyl of $C_3$–$C_4$,
halogenated loweralkanoyl of $C_2$–$C_4$ bearing on any position or positions one or more halogen atoms, each independently selected, subject to the limitation that the alpha position bear at least one substituent moiety selected from the group consisting of hydrogen and halogen of atomic weight from 35 to 127, both inclusive,
radical of the formula

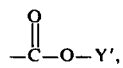

wherein Y′ represents loweralkyl of $C_1$–$C_4$ or phenyl,
benzoyl,
furoyl,
naphthoyl, or
substituted benzoyl of the formula

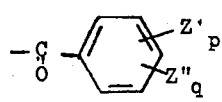

wherein each Z′ independently represents halo or nitro, Z″ represents loweralkyl of $C_1$–$C_4$ or loweralkoxy of $C_1$–$C_4$, p represents 1 or 2, q represents 0 or 1, and the sum of p and q is 1 or 2;
$R^2$ represents halogen, nitro, -$CF_3$, -$CF_2Cl$, -$CF_2H$, cyano, or loweralkylsulfonyl of $C_1$–$C_4$;
$R^3$ represents halogen;
and m represents an integer of from 0 to 2, both inclusive, subject to the limitation that when $R^2$ represents a moiety other than halogen, m is no greater than 1; or an acid addition salt thereof.

2. The compound of claim 1 which is $N^3$-trifluoroacetyl-5-chloro-2,3-pyridinediamine.

3. The compound of claim 1 which is $N^3$-trifluoroacetyl-5-cyano-2,3-pyridinediamine.

4. The compound of claim 1 which is $N^2,N^3$-bis(trifluoroacetyl)-5-chloro-2,3-pyridinediamine.

5. The compound of claim 1 which is $N^3$-trifluoroacetyl-5-trifluoromethyl-2,3-pyridinediamine.

6. The compound of claim 1 which is $N^3$-trifluoroacetyl-5-nitro-2,3-pyridinediamine.

7. The compound of claim 1 which is $N^2$-acetyl-$N^3$-trifluoroacetyl-5-trifluoromethyl-2,3-pyridinediamine.

* * * * *

UNITED STATES PATENT AND TRADEMARK OFFICE
CERTIFICATE OF CORRECTION

PATENT NO. : 3,962,263
DATED : June 8, 1976
INVENTOR(S) : George O. P. Doherty

It is certified that error appears in the above-identified patent and that said Letters Patent are hereby corrected as shown below:

Column 2, line 53, "difuoroacetyl" should be --difluoroacetyl--.

Column 4, line 3, between "with" and "mixed," insert --a--; line 18, the word "produce" should be --product--; and line 28, "2,3) Pyridinediamine" should be --2,3-PYRIDINEDIAMINE--.

Column 5, each of lines 8 and 10, "secbutylsulfonyl" should be --sec-butylsulfonyl--; line 10, the "b" should be deleted after "$N^2$-propionyl-"; and line 22, "difluoro3,4-" should read --difluoro-3,4- --.

Column 6, line 19, a closing parenthesis should be added after the word "methoxycarbonyl".

Column 7, line 56, between "or" and "the", insert --in--.

Column 8, line 17, between "general," and "broad," insert --a--; and line 53, "Liguid" should be spelled --Liquid--.

Column 9, line 14, "2,665,447" should be --2,655,447--.

Column 10, line 16, "elevation" should be --evaluation--.

Column 12, line 45, there should be a dash between the closing parenthesis and "5".

Column 14, line 6, "added" should be --heated--.

Column 15, line 13, "loweralkanoyl of $C_3$-$C_4$" should be --loweralkynoyl of $C_3$-$C_4$--.

Signed and Sealed this

Twenty-eighth Day of September 1976

[SEAL]

Attest:

RUTH C. MASON
Attesting Officer

C. MARSHALL DANN
Commissioner of Patents and Trademarks